United States Patent [19]
Ball

[11] Patent Number: 5,407,507
[45] Date of Patent: Apr. 18, 1995

[54] METHOD AND APPARATUS FOR COMBINING A TENSIONED ELASTIC MEMBER WITH A MOVING SUBSTRATE WEB

[75] Inventor: Walter K. Ball, Cincinnati, Ohio

[73] Assignee: The Procter & Gamble Company, Cincinnati, Ohio

[21] Appl. No.: 142,632

[22] Filed: Oct. 25, 1993

[51] Int. Cl.6 .................... B32B 31/10; B32B 31/18; A61F 13/15
[52] U.S. Cl. .................................. 156/163; 156/164; 156/229; 156/256; 156/264; 156/265; 156/285; 156/494; 156/496; 156/520; 156/519
[58] Field of Search ............... 156/161, 163, 164, 229, 156/494–496, 265, 285, 308.4, 520, 519, 517, 256, 264

[56] References Cited

U.S. PATENT DOCUMENTS

| | | |
|---|---|---|
| 3,003,903 | 10/1961 | Vaughan . |
| 3,694,815 | 10/1972 | Burger . |
| 4,081,301 | 3/1978 | Buell . |
| 4,284,454 | 8/1981 | Joa . |
| 4,285,747 | 8/1981 | Rega . |
| 4,293,367 | 10/1981 | Klasek et al. . |
| 4,337,771 | 7/1982 | Pieniak et al. . |
| 4,523,969 | 6/1985 | Spencer .......................... 156/229 X |
| 4,527,990 | 7/1985 | Sigl . |
| 4,563,185 | 1/1986 | Reiter . |
| 4,642,151 | 2/1987 | Coenen .............................. 156/164 |
| 4,710,189 | 12/1987 | Lash . |
| 4,735,673 | 4/1988 | Piron .................................. 156/496 |
| 4,813,946 | 3/1989 | Sabee . |
| 4,846,827 | 7/1989 | Sallee et al. . |
| 4,863,542 | 9/1989 | Oshefsky et al. . |
| 4,867,735 | 9/1989 | Wogelius . |
| 4,919,738 | 4/1990 | Ball et al. . |
| 4,925,520 | 5/1990 | Beaudoin et al. ............... 156/229 X |
| 4,943,340 | 7/1990 | Ujimoto et al. ..................... 156/496 |
| 4,968,313 | 11/1990 | Sabee . |
| 5,000,806 | 3/1991 | Merkatoris et al. ............ 156/164 X |
| 5,004,466 | 4/1991 | Uda et al. . |
| 5,171,391 | 12/1992 | Chmielewski et al. ............. 156/229 |
| 5,185,052 | 2/1993 | Chappell et al. . |
| 5,296,080 | 3/1994 | Merkatoris et al. ............ 156/164 X |
| 5,308,345 | 5/1994 | Herrin ............................ 156/164 X |

FOREIGN PATENT DOCUMENTS 0464865 8/1992 European Pat. Off. .
WO94/06384 3/1994 WIPO .

Primary Examiner—Jeff H. Aftergut
Attorney, Agent, or Firm—Ronald W. Kock; Kevin C. Johnson

[57] ABSTRACT

A method and apparatus for stretching an elastic member in cross machine direction and combining the elastic member, while held in tension, with a moving substrate web. A web of unstretched material, having elasticity across the direction of metering, is fed onto a first rotating drum at a speed slower than the surface speed of the drum. A cutter roll severs a portion of the unstretched material from its leading edge. Vacuum grippers in a drum slot beneath the elastic member support the ends of the member when it is cut from the web. Sealing dies are mounted to the surface of the vacuum grippers below the ends of the elastic member. As the first drum rotates further, the vacuum grippers are cammed axially outward within the slot to stretch the elastic member. Meanwhile, a substrate web is metered onto a second drum which rotates at the same surface speed as the first drum. The second drum rotates against the first drum but in the opposite direction. When the stretched elastic member reaches the nip point between drums, the sealing dies compression bond the ends of the stretched elastic member to the substrate web, using the second drum surface as an anvil surface. Vacuum applied to the second drum maintains the substrate web flat after the stretched elastic member is bonded and released by the vacuum grippers. A secondary sealing operation secures the stretched elastic member to the substrate web in locations other than the ends of the member before the elastic member and substrate web are allowed to contract.

15 Claims, 3 Drawing Sheets

METHOD AND APPARATUS FOR COMBINING A TENSIONED ELASTIC MEMBER WITH A MOVING SUBSTRATE WEB

FIELD OF THE INVENTION

The present invention relates to a process for elasticizing an article by bonding a tensioned elastic member to it, and more particularly to a process wherein the elastic member is held under tension in the cross machine direction as it is applied to a moving substrate. Even more particularly, the present invention relates to a process wherein the elastic member is tensioned on a rotating drum as the drum rotates.

BACKGROUND OF THE INVENTION

Elasticizing a flexible substrate, such as a sheet of cloth or plastic film, may be accomplished by attaching a tensioned elastic member to it. When the elastic member is allowed to contract, the flexible article wrinkles or shirrs to contract in dimension along with the elastic member. The article can subsequently be stretched as though it were itself elastic. This concept is used, for example, in the manufacture of disposable diapers to provide elastic waistbands for snug, leak-resistant, body fit.

There are many commercial processes for combining elastic members with substrate materials. However, reliably combining "live" or tensioned elastics, held in cross machine direction, with a continuously moving substrate web, as is required in high speed diaper-making systems, has required relatively complex methods and apparatii. For example, the substrate web may be passed through a festoon system whereby the continuously moving web is effectively indexed. That is, the substrate web is stopped for a short time along a portion of its path while the remainder of the web continues to move within a series of accumulation rolls. An elastic ribbon may then be sequentially stretched and bonded across the temporarily stationary portion of the web. Such a web handling system is necessarily large and unrealistic for the 1000 feet per minute web speeds of modem, high speed, diaper lines.

Alternatively, an elastic ribbon may be tensioned and then heat deactivated to cause it to become inelastic after it has been elongated. Because the elastic property is deactivated, the elastic can be handled without concern for contraction forces wrinkling the substrate web during bonding. Later, after the elastic has been bonded to the substrate web, a separate heat reactivation step reestablishes the elasticity of the profiled ribbon. Because of the need for heat deactivation and reactivation, elastic material choices are limited. Such processes are complicated by the fact that whenever heat is applied to polymer elastic materials, the temperature must be accurately controlled to avoid interfering with elastic properties. Also, the important properties of spring rate and percent stretch that am available for heat reactivated elastic materials are less than those available for "live" elastics which are not reactivated with heat.

Diaper elastic members are typically either polymer ribbons or laminates of multiple polymer strands combined with nonwoven sheets. Elastic members may generally be bonded to substrates in high speed continuous processes by compression bonding, thermal bonding, and adhesive bonding.

In light of the complexity of known processes for combining tensioned elastic members with moving substrate webs, and the need for generating diaper waistbands made of tensioned elastics, it is an object of the present invention to combine elastics, held in tension in the cross machine direction, with a continuously moving substrate web in a compact, high speed process.

It is a further object of the present invention to cut an unstretched elastic member from an elasticized web and stretch it in cross machine direction on the fly prior to combining the tensioned elastic to a moving substrate web.

It is yet another object of the present invention to combine a tensioned elastic member to a moving substrate web without the need for introducing external heat to the materials.

SUMMARY OF THE INVENTION

In one preferred embodiment, the present invention provides a method of combining a tensioned elastic member with a substrate web moving continuously transverse to the direction of elastic member tensioning. An unstretched elastic member is cut from the leading edge of an elastic material web. The cutting occurs against an outer surface of a first rotating drum while the leading edge of the elastic material web is supported by a pair of clamping members axially movable on the first rotating drum. The unstretched elastic member has two ends. Each end of the unstretched elastic member is gripped by one of the clamping members. Each of the clamping members has a sealing die mounted thereto beneath each of the ends of the elastic member. The clamping members are moved axially apart to stretch the unstretched elastic member while the first drum rotates, thereby forming a stretched elastic member having two ends. A substrate web is metered onto a second rotating drum. The second rotating drum rotates parallel to and has the same surface speed as the first rotating drum. The second rotating drum is supported to provide an anvil surface for the sealing dies of the first rotating drum. The ends of the stretched elastic member and the substrate web are pressed against the anvil surface by the sealing dies as the stretched elastic member and the substrate web pass between the first and second rotating drums.

In this preferred embodiment the clamping members of the first rotating drum comprise vacuum grippers. The first rotating drum has a source of vacuum communicating with each of the vacuum grippers. The vacuum is sufficient to hold the ends of the stretched elastic member after the vacuum grippers are moved axially apart. Pressing the elastic member and the substrate against the anvil surface may provide bonding in one of at least three different ways. It may exert sufficient pressure to fusion bond the ends of the stretched elastic member to the substrate web wherever the sealing dies contact the stretched elastic member and the substrate web. This method is one of compression bonding. Or the stretched elastic member may have a pressure sensitive adhesive coating enabling it to be secured to the substrate web when the stretched elastic member is pressed against the substrate web. This method is one of adhesive bonding. Or the sealing dies may be heated sufficiently to fusion bond the ends of the stretched elastic member to the substrate web wherever the sealing dies contact the stretched elastic member. This method is one of thermal bonding.

In another preferred embodiment of the present invention an apparatus for combining a tensioned elastic member with a substrate web moving continuously transverse to the direction of elastic member tensioning comprises a means for supporting and driving a first rotating drum and a second rotating drum parallel to and rotating in the opposite direction of one another. The second rotating drum is supported to provide a sealing anvil surface. Means is also provided for cutting an unstretched elastic member from the leading edge of an elastic material web. The cutting occurs against an outer surface of the first rotating drum while the leading edge of the elastic material web is supported by a pair of clamping members axially movable on the first rotating drum. The unstretched elastic member has two ends. In addition, there are means for gripping each end of the unstretched elastic member by one of the clamping members, each of the clamping members having a sealing die mounted thereto beneath each of the ends of the unstretched elastic member. A means for moving the clamping members axially apart is also provided to stretch the unstretched elastic member while the first drum rotates, thereby forming a stretched elastic member having two ends. There is also a means for metering a substrate web onto the second rotating drum. The second rotating drum has the same surface speed as the first rotating drum. Finally there is a means for sealing each of the ends of the stretched elastic member to the substrate web as the stretched elastic member and the substrate web pass between the first and second rotating drums.

In this preferred embodiment the means for moving the clamping members axially comprises stationary cam surfaces at each end of the first rotating drum. Also, the second rotating drum has vacuum holes about it in order to prevent the substrate web wrinkling in cross machine direction after the stretched elastic member is bonded to the substrate web. The second rotating drum has a source of vacuum communicating with the vacuum holes, the vacuum being sufficient to hold the substrate web against the vacuum holes. Holding the elastic member in a stretched condition enables a secondary sealing operation to bond other portions of the stretched elastic member to the substrate web.

In yet another preferred embodiment an apparatus for combining a tensioned elastic member with a substrate web moving continuously transverse to the direction of elastic member tensioning comprises a frame and drive train for supporting and driving a first rotating drum and a second rotating drum. A first rotating drum has a band of vacuum apertures about its circumference. A second rotating drum is parallel to and rotating in the opposite direction of the first rotating drum. The second rotating drum is supported against the first rotating drum to provide a sealing anvil surface at a nip point between the first and second rotating drums. A cutting roll is mounted adjacent to the first rotating drum for cutting an unstretched elastic member from the leading edge of an elastic material web held against the first rotating drum by vacuum applied to the band of vacuum apertures about the first rotating drum. The unstretched elastic member has two ends. A pair of vacuum grippers is mounted to the first rotating drum and adapted to support each end of the unstretched elastic member as the unstretched elastic member is cut from the elastic material web. Each of the vacuum grippers has a sealing die mounted thereto beneath each of the ends of the unstretched elastic member. Cam tracks are mounted to the frame for moving the vacuum grippers axially apart to stretch the unstretched elastic member when the first drum rotates, thereby forming a stretched elastic member having two ends. A substrate web is metered onto the second rotating drum. The second rotating drum has the same surface speed as the first rotating drum, such that when the stretched elastic member and the substrate web pass through the nip point between the first and second rotating drums, each of the sealing dies mounted to the vacuum grippers presses each of the ends of the stretched elastic member against the substrate web supported by the anvil surface of the second rotating drum. A compression bond is thereby generated between the ends of the stretched elastic member and the substrate web.

In this preferred embodiment the second rotating drum has vacuum holes about it in order to prevent the substrate web wrinkling in cross machine direction after the stretched elastic member is bonded to the substrate web. The second rotating drum has a source of vacuum communicating with the vacuum holes, the vacuum being sufficient to hold the substrate web against the vacuum holes. Also, a sealing roll may be adapted to press against the second rotating drum downstream from the nip point between the first and second rotating drums in order to compression bond other portions of the stretched elastic member to the substrate web.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
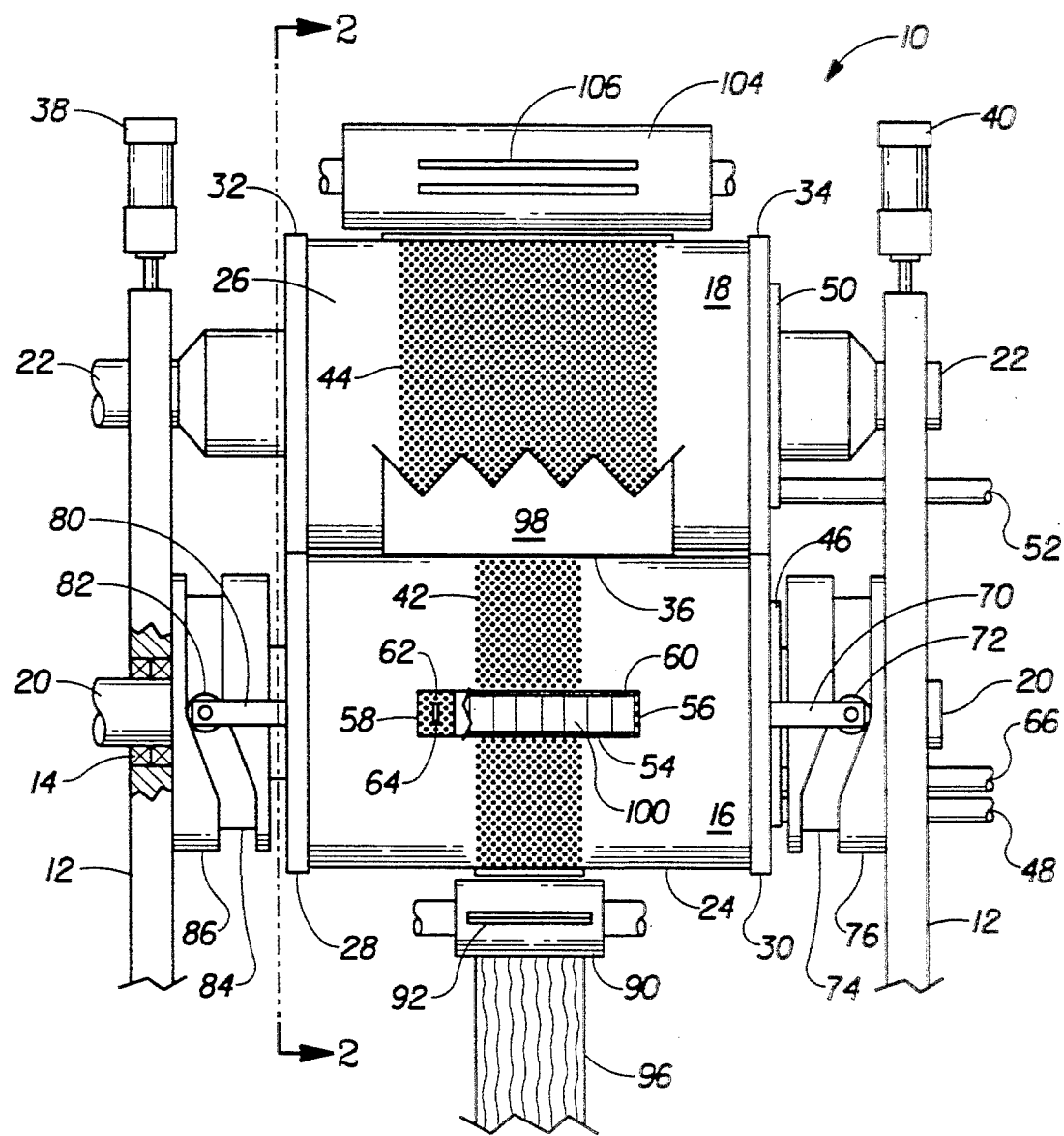
FIG. 1 is a front elevation view of a preferred embodiment of the apparatus for combining a tensioned elastic member with a moving substrate web of the present invention, disclosing two vacuum drums one above the other, a cutter roll, a sealing roll, an elastic material web entering the apparatus from below, and a substrate web entering the apparatus from above.
Figure 2:
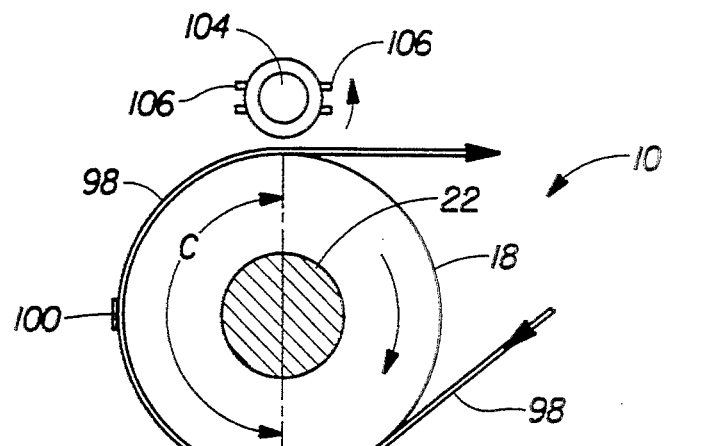
FIG. 2 is a sectioned side elevation view, taken along section line 2—2 of FIG. 1, showing the path of the elastic material web and the substrate web about the two vacuum drums, when the drums and rolls are oriented according to FIG. 1.
Figure 2:
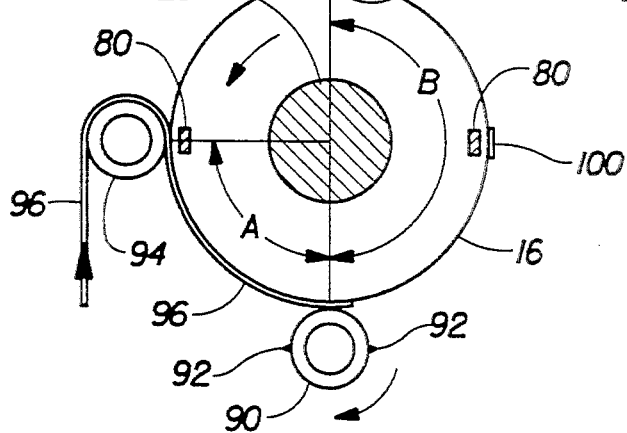

Referring now to the drawings, and more particularly to FIGS. 1 and 2, there is shown a preferred embodiment of the present invention, which provides an apparatus for combining a tensioned live elastic with a moving substrate web, and is generally indicated as 10. The apparatus 10 has a frame 12 with bearings 14 for supporting a first rotating drum 16. A second rotating drum 18 is supported by bearings not shown. The bearings supporting second rotating drum 18 slide vertically in frame 12 so that second rotating drum 18 may be loaded against first rotating drum 16, the two drums being supported parallel to one another. First and second rotating drums 16 and 18 have drive shafts 20 and 22, respectively mounted in frame bearings. Drums 16 and 18 are driven by a drive train not shown, but which is commonly known in the art. Rotating drum 18 is driven such that it rotates at the same speed but in the opposite direction from first rotating drum 16.

Drums 16 and 18 have circumferential outer surfaces 24 and 26, respectively. At each end of drums 16 and 18 are bearer rings 28, 30, 32, and 34. Bearer rings 28 and 30 of drum 16 and bearer rings 32 and 34 of drum 18 provide contacting surfaces between the drums. Preferably both drums have the same diameter bearer rings so that each drum rotates one revolution when the other rotates one revolution in order to maintain pitch registration. Because the diameters of bearer rings 28, 30, 32, and 34 are slightly greater in diameter than outer surfaces 24 and 26, a fixed gap 36 exists at the nip point between drums 16 and 18 when the bearer rings are in contact. The nip point is a term used to describe the line of contact between two cylindrical rolls. However, in this disclosure nip point refers to the gap 36 between drums 16 and 18 drawn between the nip points of bearer rings 28, 20, 32, and 34.

Holding bearer rings 28 and 30 against bearer rings 32 and 34 are air cylinders 38 and 40, which press against the sliding bearings supporting shaft 22 of the second rotating drum 18. Air cylinders 38 and 40 are mounted to frame 12 and are energized by a compressed air source not shown.

Drum 16 has a band of apertures 42 about its circumferencial surface 24 and drum 18 has a band of apertures 44 about its circumferential surface 26. Low level vacuum is applied to both bands of apertures from a source not shown and for a purpose disclosed hereinafter. Vacuum is delivered to one end of first rotating drum 16 from a stationary manifold 46 connected with pipe 48, both of which are supported by frame 12. Vacuum is delivered to one end of second rotating drum 18 from a stationary manifold 50 connected with pipe 52, both of which are also supported by frame 12.

First rotating drum 16 has two axial slots 54 centered within circumferential surface 24 and oriented 180° apart on opposite sides of drum 16. Within each slot 54 are two clamping members 56 and 58 which are preferably vacuum grippers, but which may also be mechanical clamps which are well known in the art. Vacuum grippers 56 and 58 have apertured vacuum gripping surfaces 60 and 62 tangent to surface 24. Centered within apertured vacuum gripping surfaces 60 and 62 and rising slightly above the vacuum gripping surfaces 60 and 62 are sealing dies 64. The function of vacuum grippers 56 and 58 and sealing dies 64 is discussed hereinafter. A high level vacuum is applied to vacuum grippers 56 and 58 from a vacuum source not shown. However, vacuum is delivered to drum 16 via stationary manifold 46 and pipe 66, both of which are supported from frame 12.

Extending from vacuum gripper 56 is cam follower rod 70, which is guided in bearings below the surface 24 of drum 16. Cam follower rod 70 has a cam follower 72 at one end which rides in the track 74 of a stationary barrel cam 76. As first drum 16 rotates, the shape of track 74 causes cam follower 72 to move cam follower rod 70 axially, thereby moving vacuum gripper 56 within slot 54. Similarly, extending from vacuum gripper 58 is cam follower rod 80, which is guided in bearings below the surface 24 of drum 16. Cam follower rod 80 has a cam follower 82 at one end which rides in the track 84 of a stationary barrel cam 86. As first drum 16 rotates, the shape of track 84 causes cam follower 82 to move cam follower rod 80 axially, thereby moving vacuum gripper 58 within slot 54. The purpose of this mechanism will be explained hereinafter.

Also mounted from frame 12 is a cutter roll 90 which has two axially oriented burst-cutting blades 92 connected to roll 90. Blades 92 are commonly known as flex-knives in the art. Each blade 92 is positioned 180° from the other on opposite sides of cutter roll 90. Cutter roll 90 is located adjacent first drum 16 such that surface 24 of drum 16 acts as an anvil surface for burst-cutting blades 92. The operation of the cutting roll will be explained hereinafter.

Mounted adjacent second rotating drum 18 is a sealing roll 104, which is supported by frame 12 and driven by a drive train not shown. Sealing roll 104 has sealing dies 106 positioned at 180° from each other on opposite sides of sealing roll 104. Sealing dies 106 utilize surface 26 of drum 18 as an anvil surface, and operate as will be described hereinafter. FIG. 1 also shows a portion of a substrate web 98 being metered into nip point 36 between drums 16 and 18.

Now referring to FIG. 2, the opposite rotations of first drum 16 and second drum 18 can be seen. Cutter roll 90 rotates opposite to first drum 16 and sealing roll 104 rotates opposite to second drum 18. In FIG. 2 there is shown an idler roll 94 adjacent first rotating drum 16. An elastic material web 96 is metered, from a source not shown, around idler roll 94 and onto surface 24 of drum 16. Elastic material web 96 is elastic in the cross machine direction. It is preferably less elastic along its length. Elastic material web is preferably a trilaminate made of polypropylene nonwoven outer layers having parallel natural robber strands glued intermittently in cross machine direction between the outer layers. An example of a process suitable for making an elastic material web is disclosed in U.S. Pat. No. 5,185,052 issued to Chappell et al. on Feb. 9, 1993, which is hereby incorporated by reference.

The web 96 is preferably unstretched in cross machine direction when it is metered onto first drum 16. The means for metering web 96 is not shown; however, web 96 is metered at a rate substantially slower than the speed of surface 24 of first drum 16. The speed ratio of drum 16 to web 96 is the same as the ratio of the pitch length of a diaper to the desired width of a waistband elastic member.

The drive for cutter roll 90 is not shown. However, the surface of cutter roll 90 is driven at the same surface speed as that of drum 16 when blades 92 contact surface 24 of first rotating drum 16. Cutter roll 90 rotates one revolution for every revolution of drum 16; therefore, if cutter roll 90 is smaller than drum 16, it must be driven in a fast/slow manner, as is commonly known in the art. The blades 92 of cutter roll 90 are registered with the slots 54 in drum 16 such that cutting occurs at the trailing edge of slot 54.

Figure 4:
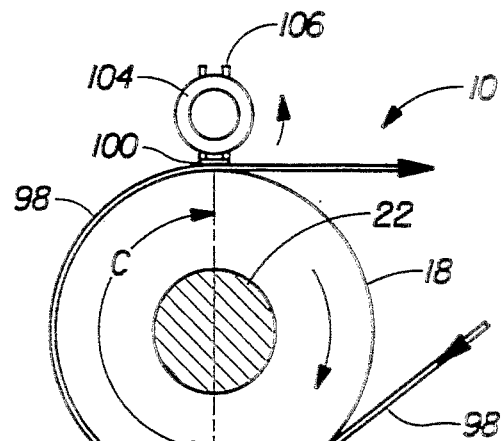
FIG. 4 is a sectioned side elevation view, taken along section line 4—4 of FIG. 3, showing the path of the elastic material web and the substrate web about the two vacuum drums, when the drums and rolls are oriented according to FIG. 3.
Figure 4:
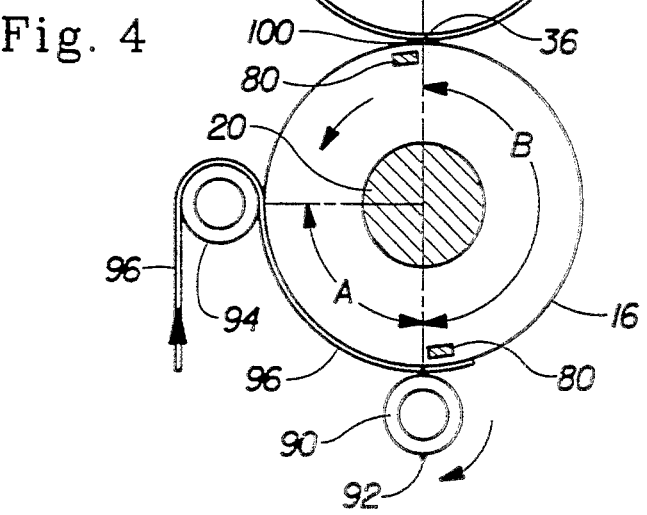

The method of making an elastic waistband member and combining it with a moving substrate web 98 is described as follows. Unstretched elastic material web 96 is metered over idler roll 94 and onto surface 24 of rotating drum 16. Vacuum manifold 46 delivers low level vacuum to the band of aperatures 42 in drum 16 at zone A located between idler roll 94 and cutter roll 90. The low level vacuum acts to hold web 96 against surface 24 of drum 16. However, because the surface speed of drum 16 is substantially greater than that of the metered web 96, web 96 slips on surface 24. Web 96 is subsequently pulled into the nip between cutter roll 90 and drum 16. The leading edge of web 96 passes the nip point and rests on vacuum grippers 56 and 58 just as blade 92 contacts the trailing edge of slot 54 in drum 16 and cuts a member of unstretched elastic 100 from web 96. This is best seen in FIG. 4. Immediately after cutting, a high level vacuum is distributed from manifold 46 to apertured surfaces 60 and 62 of vacuum grippers 56 and 58 in order to grip the ends of unstretched elastic member 100. Elastic member 100 is pulled away from slow moving elastic material web 96, once it is severed, as grippers 56 and 58 rotate with drum 16. This is known in the art as a cut and slip process.

FIG. 2 shows that the high level vacuum is applied to vacuum grippers 56 and 58 within zone B. Accordingly, elastic member 100 is transported by the vacuum grippers from the cutter roll 90 through the nip point 36 between first and second drums 16 and 18. After passing nip point 36 the high level vacuum is no longer applied so that the vacuum grippers release the elastic member. Thus, after nip point 36 there is no vacuum distributed to either band of apertures 42 or to vacuum grippers 56 and 58. In zone C shown on second vacuum drum 18, a low level vacuum is distributed to band of apertures 44 via vacuum manifold 50 to maintain control of substrate 98 after an elastic member has been bonded to it.

Figure 3:
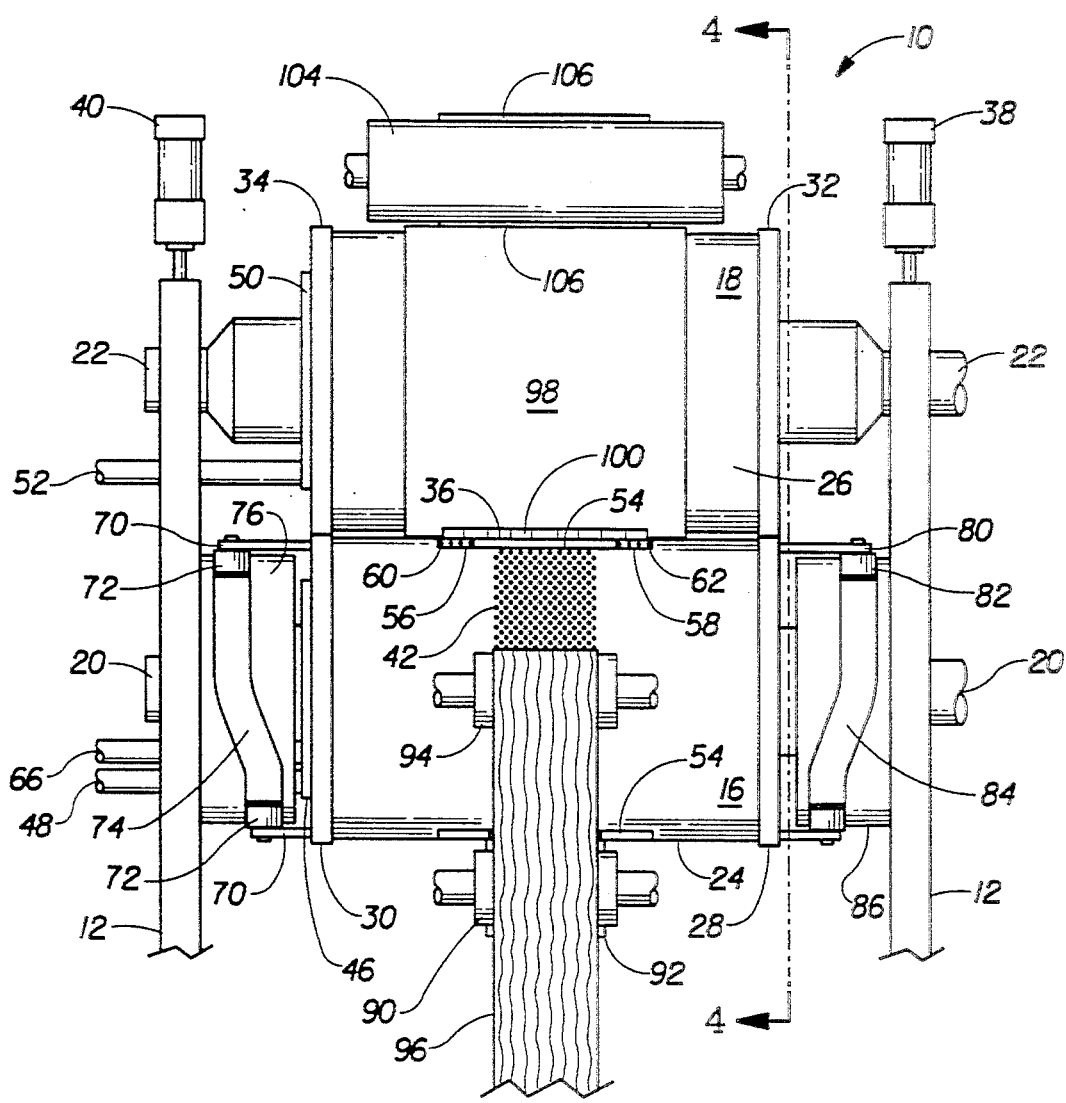
FIG. 3 is a rear elevation view of the embodiment of FIG. 1, disclosing the drums and rolls rotated 90° to their orientation shown in FIG. 1.

FIG. 3 shows the apparatus 10 from the opposite side from FIG. 1. FIG. 3 shows vacuum grippers 56 and 58 retracted toward the center of slot 54 when the cutting of unstretched elastic material web 96 occurs, such that the ends of the unstretched elastic member 100 rest on apertured surfaces 60 and 62 of the vacuum grippers. As first drum 16 rotates 180° from the cutting position to the nip 36 position, cam tracks 74 and 84 are shaped to axially move vacuum grippers 56 and 58 apart within slot 54, thereby stretching the unstretched elastic member 100. Stretched elastic member 100 is securely held to the vacuum grippers only by the high level vacuum as stretching occurs. Preferably the materials of construction of elastic member 100 have sufficiently low porosity to enable vacuum gripping to overcome any resistance to stretching member 100.

FIG. 2 shows that substrate web 98 is metered onto surface 26 of second drum 18 at a position upstream from nip point 36. Substrate web 98 is metered at the same surface speed as that of surface 26 of drum 18. As both the substrate web and the stretched elastic member pass through the nip point 36, low level vacuum is applied through band of apertures 44 on drum 18, to the full width of the substrate web. Vacuum grippers 56 and 58 have raised sealing dies 64 which press the ends of the stretched elastic member 100 against the substrate web backed by surface 26 of second drum 18. Thus, surface 26 is a sealing anvil surface for sealing dies 64. The method of sealing the ends of the elastic member 100 to substrate web 98 is preferably by compression bonding, whereby high contact pressure causes polymeric materials to flow together. An example of a suitable compression bonding process is disclosed in U.S. Pat. No. 4,919,738 issued to Ball et al. on Apr. 24, 1990, which is hereby incorporated by reference. However, other bonding methods, such as heating the sealing dies to cause thermal fusion-bonding, or applying pressure sensitive adhesive to the outer surface of the stretched elastic member, may be used.

Sealing must occur almost instantly so that high operating speed may be attained. In order to repeatedly achieve the high contact pressures necessary for compression bonding, bearer rings 28, 30, 32, and 34 are preferably discontinuous at the vacuum grippers so that the full loading of the air cylinders 38 and 40 is applied to the sealing dies. The width of the bearer ring discontinuity is preferably no more than the width of the sealing die, and the sealing die preferably has a surface diameter such that there is minimal bounce between drums during the transition from bearer ring contact to die/anvil surface contact and back again.

After sealing is complete, substrate web 98 continues to travel around second drum 18 with a stretched elastic member 100 attached at every diaper pitch length.

Sealing roll 104 is used to further bond stretched elastic member 100 to substrate web 98, as needed for an elastic waistband for a diaper. Surface 26 of drum 18 serves as the anvil sealing surface for sealing roll 104. Compression bonding is the preferred sealing method, although other sealing methods are within the scope of this invention. Sealing roll 104 is either sized the same as drum 18 or if smaller, it has a fast/slow drive system, as is commonly known in the art, so that its surface speed matches that of drum 18 during sealing contact, but otherwise it is slower than that of drum 18. Sealing contact of roll 104 is registered with the vacuum grippers of drum 16 so that contact occurs only where elastic member 100 is bonded at its ends to the substrate web 98. The bonding pattern is determined by the shape of the raised die surfaces 106 on sealing roll 104.

FIG. 4 is the same as FIG. 2 except that roll positions are 90° out of phase. FIG. 4 shows elastic material web 96 being cut at the same time as vacuum grippers have just bonded a stretched elastic member to the substrate web 98 and secondary bonding of the elastic member to the substrate web occurs.

In a particularly preferred embodiment of the present invention, the two rotating drums 16 and 18 are 288.8 mm in diameter and they rotate at 300 rpm. The drums are constructed of steel and have a width dimension of 355.6 mm. The elastic material web is a tri-laminate having two outside layers of pleated polypropylene non-woven and an elastomeric center web, compression bonded together. The elastic material web is preferably 92 mm wide. The substrate web is polypropylene non-woven and is 322.6 mm wide. The air cylinders loading the drums together preferably apply a load of 6895 BAR to the effective sealing area. The sealing dies 64 of the vacuum grippers are raised 0.076 mm above surface 24 of drum 16. The metering speed of web 96 is 14% of the surface speed of drum 16. Elastic member 100 is cut to 63.5 mm width.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A method of combining a tensioned elastic member with a substrate web moving continuously transverse to a direction of elastic member tensioning, said method comprising the steps of:
   a) cutting an unstretched elastic member from a leading edge of an elastic material web, said cutting step occurring against an outer surface of a first rotating drum while said leading edge of said elastic material web is supported by a pair of clamping members axially movable on said first rotating drum, said unstretched elastic member having two ends;

b) gripping each end of said unstretched elastic member by one of said clamping members, each of said clamping members having a sealing die mounted thereto beneath each of said ends of said elastic member;

c) moving said clamping members axially apart to stretch said unstretched elastic member while said first drum rotates, thereby forming a stretched elastic member having two ends;

d) metering a substrate web onto a second rotating drum, said second rotating drum rotating parallel to and having a same surface speed as said first rotating drum, said second rotating drum supported to provide an anvil surface for said sealing dies of said first rotating drum; and e) pressing said ends of said stretched elastic member and said substrate web against said anvil surface by said sealing dies as said stretched elastic member and said substrate web pass between said first and second rotating drums.

2. The method of claim 1 wherein said clamping members of said first rotating drum comprise vacuum grippers, said first rotating drum having a source of vacuum communicating with each of said vacuum grippers, said vacuum being sufficient to hold said ends of said stretched elastic member after said vacuum grippers are moved axially apart.

3. The method of claim 1 wherein said pressing step exerts sufficient pressure to fusion bond said ends of said stretched elastic member to said substrate web wherever said sealing dies contact said stretched elastic member, said bonding being compression bonding.

4. The method of claim 1 wherein said stretched elastic member has a pressure sensitive adhesive coating enabling it to be secured to said substrate web when said stretched elastic member is pressed against said substrate web, said securing being adhesive bonding.

5. The method of claim 1 wherein said sealing dies are heated sufficiently to fusion bond said ends of said stretched elastic member to said substrate web wherever said sealing dies contact said stretched elastic member, said bonding being thermal bonding.

6. An apparatus for combining a tensioned elastic member with a substrate web moving continuously transverse to a direction of elastic member tensioning, said apparatus comprising:

a) means for supporting and driving a first rotating drum and a second rotating drum parallel to and rotating in an opposite direction of one another, said second rotating drum supported to provide a sealing anvil surface;

b) means for cutting an unstretched elastic member from a leading edge of an elastic material web, said cutting occurring against an outer surface of said first rotating drum while said leading edge of said elastic material web is supported by a pair of clamping members axially movable on said first rotating drum, said unstretched elastic member having two ends;

c) means for gripping each end of said unstretched elastic member by one of said clamping members, each of said clamping members having a sealing die mounted thereto beneath each of said ends of said unstretched elastic member;

d) means for moving said clamping members axially apart to stretch said unstretched elastic member while said first drum rotates, thereby forming a stretched elastic member having two ends;

e) means for metering a substrate web onto said second rotating drum, said second rotating drum having a same surface speed as said first rotating drum; and f) means for sealing each of said ends of said stretched elastic member to said substrate web by said sealing dies as said stretched elastic member and said substrate web pass between said first and second rotating drums.

7. The apparatus of claim 6 wherein said clamping members of said first rotating drum comprise vacuum grippers, said first rotating drum having a source of vacuum communicating with each of said vacuum grippers, said vacuum being sufficient to hold said ends of said stretched elastic member after said vacuum grippers are moved axially apart.

8. The apparatus of claim 6 wherein said sealing dies exert sufficient pressure to fusion bond said ends of said stretched elastic member to said substrate web wherever said sealing dies contact said stretched elastic member, said apparatus providing compression bonding.

9. The apparatus of claim 6 wherein said stretched elastic member has a pressure sensitive adhesive coating enabling it to be secured to said substrate web when said stretched elastic member is pressed against said substrate web, said apparatus providing adhesive bonding.

10. The apparatus of claim 6 wherein said sealing dies are heated sufficiently to fusion bond said ends of said stretched elastic member to said substrate web wherever said sealing dies contact said stretched elastic member, said apparatus providing thermal bonding.

11. The apparatus of claim 6 wherein said means for moving said clamping members comprises axially stationary cam surfaces at each end of said first rotating drum.

12. The apparatus of claim 6 wherein said second rotating drum has vacuum holes about it in order to prevent said substrate web wrinkling in cross machine direction after said stretched elastic member is bonded to said substrate web, said second rotating drum having a source of vacuum communicating with said vacuum holes, said vacuum being sufficient to hold said substrate web against said vacuum holes.

13. An apparatus for combining a tensioned elastic member with a substrate web moving continuously transverse to a direction of elastic member tensioning, said apparatus comprising:

a) a frame and drive train for supporting and driving a first rotating drum and a second rotating drum;

b) a first rotating drum having a band of vacuum apertures about its circumference;

c) a second rotating drum parallel to and rotating in an opposite direction of said first rotating drum, said second rotating drum supported against said first rotating drum to provide a sealing anvil surface at a nip point between said first and second rotating drums;

d) a cutting roll mounted adjacent said first rotating drum for cutting an unstretched elastic member from a leading edge of an elastic material web held against said first rotating drum by vacuum applied to said band of vacuum apertures about said first rotating drum, said unstretched elastic member having two ends;

e) a pair of vacuum grippers mounted to said first rotating drum and adapted to support each end of said unstretched elastic member as said unstretched elastic member is cut from said elastic material web, each of said vacuum grippers having a sealing die mounted thereto beneath each of said ends of said unstretched elastic member;

f) cam tracks mounted to said frame for moving said vacuum grippers axially apart to stretch said unstretched elastic member when said first drum rotates, thereby forming a stretched elastic member having two ends;

g) means for metering a substrate onto said second rotating drum, said second rotating drum having a same surface speed as said first rotating drum, such that when said stretched elastic member and said substrate web pass through said nip point between said first and second rotating drums, each of said sealing dies mounted to said vacuum grippers presses each of said ends of said stretched elastic member against said substrate web supported by said anvil surface of said second rotating drum in order to compression bond said ends of said stretched elastic member to said substrate web.

14. The apparatus of claim 13 wherein said second rotating drum has vacuum holes about it in order to prevent said substrate web wrinkling in cross machine direction after said stretched elastic member is bonded to said substrate web, said second rotating drum having a source of vacuum communicating with said vacuum holes, said vacuum being sufficient to hold said substrate web against said vacuum holes.

15. The apparatus of claim 13 further comprising a sealing roll adapted to press against said second rotating drum downstream from said nip point between said first and second rotating drums in order to compression bond other portions of said stretched elastic member to said substrate web.

* * * * *